United States Patent [19]
Schriver et al.

[11] Patent Number: 5,562,851
[45] Date of Patent: Oct. 8, 1996

[54] SULFUR-CONTAINING CARBONATE REACTION PRODUCTS AS LUBRICATING OIL ANTIWEAR ADDITIVES

[75] Inventors: George W. Schriver, Somerville; James S. Puckace, Perrineville, both of N.J.

[73] Assignee: Exxon Chemical Patents Inc., Linden, N.J.

[21] Appl. No.: 361,086

[22] Filed: Dec. 21, 1994

[51] Int. Cl.$^6$ .................... C10M 135/28; C10M 135/26
[52] U.S. Cl. .................... 508/462; 558/275; 558/276; 508/543; 508/565
[58] Field of Search .................... 252/48.2, 48.6, 252/47.5; 558/275, 276

[56] References Cited

U.S. PATENT DOCUMENTS

| | | | |
|---|---|---|---|
| 3,275,674 | 9/1966 | Bottenbruch et al. | 558/276 |
| 3,517,029 | 6/1970 | Johnson | 558/276 |
| 3,627,810 | 12/1971 | Chang | 260/463 |
| 4,604,242 | 8/1986 | Harley et al. | 558/260 |
| 4,968,829 | 11/1990 | Henrick | 558/275 |
| 5,284,592 | 2/1994 | Aberkane et al. | 252/48.6 |

FOREIGN PATENT DOCUMENTS

| | | |
|---|---|---|
| 0089709A1 | 9/1983 | European Pat. Off. . |
| 0482693A1 | 4/1992 | European Pat. Off. . |
| 4258693 | 2/1991 | Japan . |
| 4258694 | 2/1991 | Japan . |
| 1353249 | 5/1974 | United Kingdom . |
| WO92/10462 | 6/1992 | WIPO . |

OTHER PUBLICATIONS

CA 27029C, vol. 69, 1968 Kalutskii et al.
CA 72344g, vol. 76, 1972 Boehme et al.

*Primary Examiner*—Jerry D. Johnson
*Attorney, Agent, or Firm*—T. J. Shatynski

[57] ABSTRACT

This invention provides sulfur-containing carbonate reaction product additives which are useful as phosphorus-free antiwear additives in lubricating oils, particularly automatic transmission fluids.

11 Claims, No Drawings

SULFUR-CONTAINING CARBONATE REACTION PRODUCTS AS LUBRICATING OIL ANTIWEAR ADDITIVES

BACKGROUND OF THE INVENTION

1. Field of Invention

This invention concerns sulfur-containing carbonate reaction products and their use as antiwear additives in lubricating oils, particularly automatic transmission fluids.

2. Description of Related Art

Additives for lubricating oils perform an important role in tailoring a finished fluid to meet specific performance criteria set by equipment manufacturers. Typically, wear of moving equipment parts is controlled by phosphorus-containing compounds. However, these compounds may adversely affect other characteristics desirous in lubricating oils such as friction performance and silicone-seal compatibility. Therefore, under certain circumstances, it may be advantageous to avoid use of phosphorus-containing compounds. Additionally, there is a continuing search for new antiwear additives which are inexpensive to produce and, environmentally benign, and compatible with conventional lubrication oil additives. The additives of this invention offer one response to these problems.

GB 1,353,249 discloses that carbonic acid esters of the following formula are useful lubricants and lubricant additives:

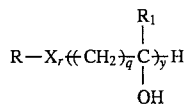

where:

$R^1$ and $R^2$ are independently a hydrogen atom, or an alkyl, alkenyl, aralkyl, aryl, acyl, alkoxy-carbonyl or aryloxy-carbonyl group;

n is a number from 2 to 300; and

X is an alkylene radical which contains 3 or more, preferably 3 to 18 carbon atoms in the main chain, an alkylene radical which contains 3 or more, preferably 3 to 18 carbon atoms in the main chain and is interrupted by one or more heteroatoms or by one or more carboxylic ester, carbamoyl, urethane, urea or tertiary amino groups; or X is a cycloalkylene, aralkylene or arylene radical.

The heteroatoms described include oxygen, sulfur, and nitrogen. However, since n=2, the claimed carbonic acid esters contain at least 2 carbonate radicals formed by alcohol exchange reactions using diols. Additionally, there is nothing in this reference to suggest the lubricating oil additives of this invention.

SUMMARY OF THE INVENTION

One embodiment of this invention concerns an oil-soluble additive, wherein the additive comprises the reaction product of a carbonylating agent and an alcohol, the alcohol being at least one thioalcohol, or, at least one thioalcohol and one sulfur-free alcohol, represented by (I) or (II), where (I) and (II) are:

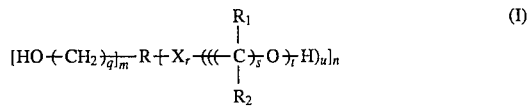

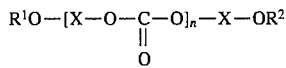

where:

m+n is an integer from 1 to 4;

m is O or an integer from 1 to 4;

n is O or an integer from 1 to 4;

q is O or an integer from 1 to 6;

R is a $C_1$–$C_{50}$ hydrocarbyl group in structure (I), and is a $C_1$–$C_{50}$ hydrocarbyl group or hydrogen in structure (II);

X is sulfur, oxygen, nitrogen, or —$CH_2$—;

r is O, or an integer from 1 to 5 providing when X is oxygen or nitrogen, r is 1, when X is sulfur, r is 1 to 3, when X is —$CH_2$—, r is 1 to 5;

s is O, or an integer from 1 to 5;

t is O, or an integer from 1 to 12;

u is O, or an integer from 1 to 2 providing when X is sulfur, oxygen, or —$CH_2$—, u is 1, when X is nitrogen, u is 1 or 2;

y is O, or an integer from 1 to 10; and $R_1$ and $R_2$ are independently a $C_1$–$C_6$ alkyl, cycloalkyl, aryl, $C_1$–$C_6$ alkyl-substituted aryl, or hydrogen.

Another embodiment of this invention relates to a lubricating oil additive comprising the structure (III):

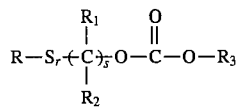

where:

R is alkyl or aryl, or substituted alkyl or aryl;

r is 1 to 3;

$R_1$, and $R_2$ are independently hydrogen, $C_1$–$C_6$ alkyl, cycloalkyl, aryl, or $C_1$–$C_6$ alkyl-substituted aryl;

s is an integer from 1 to 5; and

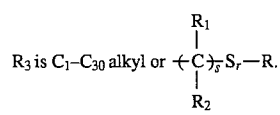

Further embodiments of this invention include lubricating oils and lubricating oil concentrates containing the additives of this invention.

Another embodiment is a method of lubricating surfaces subject to mutual wear where the lubricating fluid contains the additives of this invention in an amount effective to lessen wear of the surfaces.

An advantage of this invention is that excellent antiwear benefits are achievable while being compatible with other lubrication oil additives particularly, without detrimentally affecting the antioxidency properties of additive packages.

DETAILED DESCRIPTION OF THE INVENTION

The sulfur-containing carbonate reaction products of this invention are made by reacting at least one thioalcohol, or, at least one thioalcohol and at least one sulfur-free alcohol, with a carbonylating agent, such as a lower molecular weight dialkyl carbonate. Details concerning suitable thioalcohols, sulfur-free alcohols, carbonylating agents, and methods of preparing this invention's additives follow.

Thioalcohols and Sulfur-Free Alcohols

The thioalcohols and sulfur-free alcohols represented by structures (I) and (II) form a broad description of alcohols useful in this invention. It should be noted that the hydrocarbyl groups represented by R may be straight-chained, branched, or cyclic. Representative hydrocarbyl groups within this definition include alkyl, alkenyl, cycloalkyl, aralkyl, alkaryl, aryl, and their hetero-containing analogs.

Among the suitable alcohols within structure (I) are alkoxylated alcohols ($s \geq 1$ and $t \geq 1$) and alkoxylated polyhydric alcohols ($s \geq 1$; $t \geq 1$; and $m+n+u \geq 2$), and mixtures thereof.

Examples of particularly useful alkoxylated alcohols are nonylphenol pentaethoxylate, pentapropoxylated butanol, hydroxyethyl octyl sulfide, and diethoxylated dodecyl mercaptan.

Examples of particularly useful alkoxylated polyhydric alcohols are oleylamine tetraethoxylate, 5-hydroxy- 3-thiopentanol triethoxylate, thiobisethanol, diethoxylated tallowamine, dithiodiglycol, tetrapropoxylated cocoamine, diethylene glycol, and 1,7-dihydroxy- 3,5-dithioheptane.

Among the suitable alcohols within structure (II) are the polyhydric alcohols ($y \geq 2$). Examples of particularly useful polyhydric alcohols are pentaerythritol, 1-phenyl-2,3-propanediol, polyvinyl alcohol, 1,2-dihydroxy hexadecane and 1,3-dihydroxy octadecane.

A particularly useful combination of alcohols are those represented by (IV), (V), and mixtures thereof, where (IV) and (V) are:

$$A\text{—OH} \quad\quad\quad\quad (IV)$$

and $$OH\text{—}B\text{—}OH \quad\quad\quad\quad (V)$$

where:

A is

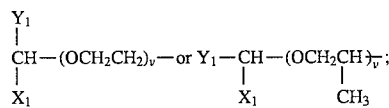

$X_1$ is H or $R_4SCH_2$—;
$Y_1$ is

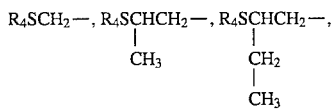

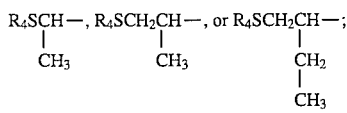

v is 0 or an integer from 1–12;

B is —$CH_2CH_2SCH_2CH_2$—, —$CH_2CH_2SSCH_2CH_2$— or

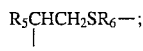

and $R_4$ and $R_5$ are the same or different and are H or a hydrocarbyl group containing up to 50 carbon atoms. $R_6$ is a hydrocarbyl group containing up to 50 carbon atoms.

The $R_4$, $R_5$, and $R_6$ groups of the alcohols (IV) and (V) are hydrocarbyl groups which may be straight-chained, branched, or cyclic. Representative hydrocarbyl groups include alkyl, alkenyl, cycloalkyl, aralkyl, alkaryl, and their hetero-containing analogs.

The hetero-containing hydrocarbyl groups may contain one or more heteroatoms. A variety of heteroatoms can be used and are readily apparent to those skilled in the art. Suitable heteroatoms include, but are not limited to, nitrogen, oxygen, phosphorus, and sulfur. Preferred heteroatoms are oxygen and sulfur, with sulfur atoms the most preferred.

When the hydrocarbyl group is alkyl, straight-chained alkyl groups are preferred—typically those that are about $C_2$ to $C_{18}$, preferably about $C_4$ to $C_{12}$, most preferably about $C_6$ to $C_{10}$ alkyl. When the hydrocarbyl group is alkenyl, straight-chained alkenyl groups are preferred—typically those that are about $C_3$ to $C_{18}$, preferably about $C_4$ to $C_{12}$, most preferably about $C_6$ to $C_{10}$ alkenyl. When the hydrocarbyl group is cycloalkyl, the group typically has about 5 to 18 carbon atoms, preferably about 5 to 16, most preferably about 5 to 12. When the hydrocarbyl group is aralkyl or alkaryl, the aryl portion typically contains about $C_6$ to $C_{12}$, preferably 6 carbon atoms, and the alkyl portion typically contains about 0 to 18 carbon atoms, preferably 1 to 10.

Straight-chained hydrocarbyl groups are preferred over branched or cyclic groups. However, if the hydrocarbyl group constitutes the less preferred cycloalkyl group, it may be substituted with a $C_1$ to $C_{18}$ straight-chained alkyl group, preferably $C_2$ to $C_8$.

Representative examples of suitable hydrocarbyl groups for alcohols (IV) and (V) include methyl, ethyl, propyl, butyl, pentyl, hexyl, heptyl, octyl, 2-ethylhexyl, isooctyl, tertiary-octyl, nonyl, isononyl, tertiary-nonyl, secondary-nonyl, decyl, isodecyl, undecyl, dodecyl, tridecyl, palmityl, stearyl, isostearyl, octenyl, nonenyl, decenyl, dodecenyl, oleyl, linoleyl and linolenyl, cyclooctyl, benzyl, octylphenyl, dodecylphenyl, and phenyloctyl.

The preferred hydrocarbyl groups for alcohol (IV) are hexyl, octyl, decyl, and dodecyl. The preferred hydrocarbyl groups for alcohol (V) are, for $R_5$: methyl, ethyl, and propyl; and, for $R_6$: methylene, ethylene, propylene, and (methyl) ethylene.

Alcohols (IV) and (V) may be prepared by conventional methods widely known in the art. For example, a thioalcohol is produced by oxyalkylation of a mercaptan containing the desired hydrocarbyl group. Suitable oxyalkylating agents include alkylene oxides such as ethylene oxide, propylene oxide, butylene oxide, and mixtures thereof. The most preferred alkylene oxide is ethylene oxide. Thus, the preferred thioalcohol may be prepared by the following reaction equation:

$$RSH + \text{Ethylene Oxide} \rightarrow RSCH_2CH_2OH \quad\quad (VI)$$

where R is defined above.

To produce the desired alcohol, a more preferred reaction route is:

$$RCH=CH_2 + HSR_2OH \rightarrow RCH_2CH_2SR_2OH \quad\quad (VII)$$

wherein R and $R_2$ are described above. Reaction equation (VII) is preferred because it yields a higher percentage of the desired alcohol whereas reaction equation (VI) may produce a single alcohol of the formula $RS(CH_2CH_2O—)_n—H$, where $n>1$, or a mixture of alcohols where $n>1$ and varies.

Carbonylating Agents

Generally, any carbonylating agent is suitable for use in this invention provided it is capable of forming a carbonate.

Suitable carbonylating agents include lower molecular weight dihydrocarbyl carbonates such as dialkyl carbonates, dicycloaliphatic carbonates, diaryl, or di-(aryl-substituted aliphatic) carbonates.

Examples of the dialkyl carbonates are dimethyl carbonate, diethyl carbonate, dipropyl carbonate, dibutyl carbonate, dipentyl carbonate, dihexyl carbonate, diheptyl carbonate, dioctyl carbonate, and dinonyl carbonate. The preferred carbonates from this group are dimethyl carbonate and diethyl carbonate.

Examples of dicycloaliphatic carbonates are dicyclopropyl carbonate, dicyclobutyl carbonate, dicyclopentyl carbonate, dicyclohexyl carbonate, dicycloheptyl carbonate, and dicyclooctyl carbonate. Preferred from this group is dicyclohexyl carbonate.

Examples of diaryl and di-(aryl-substituted aliphatic) carbonates are dibenzyl carbonate, diphenyl carbonate, di-2-phenylethyl carbonate, and the like. The preferred carbonate from this group is diphenyl carbonate.

While all of the foregoing compounds may be used as a carbonylating agent in this invention, the most preferred compound is dimethyl carbonate.

Sulfur-Containing Carbonate Reaction Product Formation

The sulfur-containing carbonate reaction product of this invention may be prepared by methods well known in the art.

A particularly useful way of producing this invention's reaction product is by an "exchange reaction." For example, when it is desired to make a thioalkyl carbonate, the thioalkyl substituent of the thioalcohol is "exchanged" for a lower molecular weight hydrocarbyl group of a dihydrocarbyl carbonate to form the thioalkyl carbonate. Typically, dimethyl carbonate is used as the dialkyl carbonate reactant.

The "exchange reaction" is typically performed in the presence of a catalyst. Many catalysts are suitable to effect this reaction. Suitable catalysts include bases such as alkali metal hydroxide and resin-bound amine bases. A particularly useful catalyst is Amberlyst A-21®. This catalyst is commercially available through Rohm and Haas Company.

The relative starting ratios of carbonylating agent to thioalcohol (or thioalcohol and alcohol) range from 1:1 to 10:1, preferably 1:1 to 3:1, most preferably 2:1. However, these relative proportions are not contemplated to limit other relative proportions where the benefits of this invention are achieved.

This process may be performed at any temperature at which the reaction proceeds. Preferable temperatures are between about 50° to 125° C., most preferably about 125° C.

This process may be performed at any pressure which encourages the rate of reaction and ease of separation of the alcohol by-product and sulfur-containing carbonate. Preferable pressures are between about 0 to 10 atmospheres, most preferably about 1 atmospheres.

The "exchange reaction" produces an alcohol (methanol in the case of dimethyl carbonate) as a by-product. Higher yields of sulfur-containing carbonate products are attainable when the alcohol by-product is removed. When the alcohol by-product is not removed or when a mixture of thioalcohol or alcohol reactants are used, this method of synthesis usually results in a mixture of sulfur-containing carbonates.

The product of the "exchange reaction" may be vacuum stripped to increase the yield of sulfur-containing carbonates in the reaction product. Typically, vacuum levels of less than 1 mm mercury at temperatures ranging from about 100° to 140° C. are satisfactory to increase the thiocarbonate yield.

The following summary shows typical reaction product contents obtained by the "exchange reaction" process and subsequent vacuum stripping as measured by carbon-13 nuclear magnetic resonance (C-13 NMR) spectrometry resulting from the reaction of hydroxyethyl octyl sulfide with dimethyl carbonate:

| Component | Amt in wt % by Exchange Reaction | Amt in wt % by Subsequent Vacuum Stripping |
|---|---|---|
| Hydroxyethyl Octyl Sulfide | 20–40 | 10–30 |
| Dimethyl Carbonate | 2–7 | 1–4 |
| Methyl, Octylthioethyl Carbonate | 15–40 | 10–25 |
| Bis (Octylthioethyl) Carbonate | 15–40 | 30–70 |

Other methods for forming the additives of this invention involve reactions of thioalcohols with activated carboxylating reagents. Examples of these reagents include phosgene ($COCl_2$), diphenyl carbonate, and methyl chloroformate. Under proper conditions, these carbonate-forming reactions can be controlled to introduce only one alcohol moiety per carbonyl group. This method of preparation allows the formation of unsymmetrical carbonates, i.e., carbonates which may contain two different thio-containing substituents or one thio-containing and one thio-free substituent.

The additives of this invention may be added to a lubricating oil basestock in an amount sufficient to impart anti-wear properties. The typical range is 0.05 to 2.0 weight percent of 100% active ingredient, preferably 0.2 to 1.0 weight percent, most preferably 0.3 to 0.7 weight percent.

It may be desirable to include a source of boron with the complex of this invention in the lubrication oil basestock. The presence of boron tends to lessen the deterioration of silicone-based seals. The boron source may be present in the form of borated dispersants, borated amines, borated alcohols, borated esters, or alkyl borates.

Accordingly, by adding an effective amount of this invention's additive to a lubricating oil and then placing the resulting lubrication oil within a lubrication system, the oil will inhibit wear in metal-to-metal contact as well as in metal-to-nonmetal contact (i.e., nonmetal composites: paper/phenolic resins, graphite/paper/phenolic resins, KEVLAR®/paper resins, etc.).

The lubrication oil basestock may contain one or more additives to form a fully formulated lubricating oil. Such lubricating oil additives include corrosion inhibitors, detergents, pour-point depressants, antioxidants, extreme pressure additives, viscosity improvers, friction modifiers, and the like. These additives are typically disclosed in, for example, "Lubricant Additives" by C. V. Smalheer and R. Kennedy Smith, 1967, pp. 1–11 and in U.S. Pat. No. 4,105,571, the disclosures of which are incorporated herein by reference. A fully formulated lubricating oil normally contains from about 1 to about 20 weight % of these additives. Borated or unborated dispersants may also be included as additives in the oil, if desired. However, the precise additives used (and their relative amounts) will depend upon the particular application of the oil. Contemplated applications for formulations of this invention include passenger car motor oils, gear oils, industrial oils, lubricating oils, and power transmission fluids, especially automatic transmission fluids and tractor hydraulic fluids. The following list shows representative amounts of additives in lubrication oil formulations:

| Additive | (Broad) Wt. % | (Preferred) Wt. % |
| --- | --- | --- |
| VI Improvers | 1–12 | 1–4 |
| Corrosion Inhibitor/Passivators | 0.01–3 | 0.01–1.5 |
| Anti-Oxidants | 0.01–5 | 0.01–1.5 |
| Dispersants | 0.10–10 | 0.1–8 |
| Anti-Foaming Agents | 0.001–5 | 0.001–1.5 |
| Detergents | 0.01–6 | 0.01–3 |
| Anti-Wear Agents | 0.001–5 | 0.001–1.5 |
| Pour Point Depressants | 0.01–2 | 0.01–1.5 |
| Seal Swellants | 0.1–8 | 0.1–6 |
| Friction Modifiers | 0.01–3 | 0.01–1.5 |
| Lubricating Base Oil | Balance | Balance |

Particularly suitable detergent additives for use with this invention include ash-producing basic salts of Group I (alkali) or Group II (alkaline) earth metals and transition metals with sulfonic acids, carboxylic acids, or organic phosphorus acids.

Particularly suitable types of antioxidant for use in conjunction with the additives of this invention are the amine-containing and hydroxy aromatic-containing antioxidants. Preferred types of these antioxidants are alkylated diphenyl amines and substituted 2,6 di-t-butyl phenols.

The antiwear properties of this invention's additives may be tailored with conventional antiwear additives. Generally, these additives are sulfur- and/or phosphorus-containing compounds. Examples of such compounds are zinc dialkyl dithiophosphates, triaryl phosphites and phosphates, phosphorized succinimides, etc. However, excellent antiwear properties are achievable with the additives of this invention in the absence of sulfur and/or phosphorus-containing antiwear compounds.

The additive of this invention may also be blended to form a concentrate. A concentrate will generally contain a major portion of this invention's additive together with other desired additives and a minor amount of lubrication oil or other solvent. The additive of this invention and desired additives (i.e., active ingredients) are provided in the concentrate in specific amounts to give a desired concentration in a finished formulation when combined with a predetermined amount of lubrication oil. The collective amounts of active ingredient in the concentrate typically are from about 0.2 to 50, preferably from about 0.5 to 20, most preferably from 2 to 20 weight % of the concentrate, with the remainder being a lubrication oil basestock or a solvent.

Suitable lubrication oil basestocks can be derived from natural lubricating oils, synthetic lubricating oils, or mixtures thereof. In general, the lubricating oil basestock will have a viscosity in the range of about 5 to about 10,000 mm$^2$/s (cSt) at 40° C., although typical applications will require an oil having a viscosity ranging from about 10 to about 1,000 mm$^2$/s (cSt) at 40° C.

Natural lubricating oils include animal oils, vegetable oils (e.g., castor oil and lard oil), petroleum oils, mineral oils, and oils derived from coal or shale.

Synthetic oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes), etc., and mixtures thereof); alkylbenzenes (e.g., dodecylbenzenes, tetradecylbenzenes, dinonylbenzenes, di(2-ethylhexyl)benzene, etc.); poly-phenyls (e.g., biphenyls, terphenyls, alkylated polyphenyls, etc.); alkylated diphenyl ethers, alkylated diphenyl sulfides, as well as their derivatives, analogs, and homologs thereof; and the like.

Synthetic lubricating oils also include alkylene oxide polymers, interpolymers, copolymers, and their derivatives where the terminal hydroxyl groups have been modified by esterification, etherification, etc. This class of synthetic oils is exemplified by polyoxyalkylene polymers prepared by polymerization of ethylene oxide or propylene oxide; the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500); and mono- and poly-carboxylic esters thereof (e.g., the acetic acid esters, mixed $C_3$–$C_8$ fatty acid esters, and $C_{13}$ oxo acid diester of tetraethylene glycol).

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, di-ethylene glycol monoether propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, and the like. Synthetic hydrocarbon oils are also obtained from hydrogenated oligomers of normal olefins.

Silicone-based oils (such as the polyalkyl-, polyaryl-, polyalkoxy-, or polyaryloxy-siloxane oils and silicate oils) comprise another useful class of synthetic lubricating oils. These oils include tetraethyl silicate, tetraisopropyl silicate, tetra-(2-ethylhexyl) silicate, tetra-(4-methyl-2-ethylhexyl) silicate, tetra(p-tert-butylphenyl) silicate, hex-(4-methyl-2-pentoxy)-disiloxane, poly(methyl)-siloxanes and poly(methylphenyl) siloxanes, and the like. Other synthetic lubricating oils include liquid esters of phosphorus-containing acids (e.g., tricresyl phosphate, trioctyl phosphate, and diethyl ester of decylphosphonic acid), polymeric tetrahydroforans, polyalphaolefins, and the like.

The lubricating oil may be derived from unrefined, refined, rerefined oils, or mixtures thereof. Unrefined oils are obtained directly from a natural source or synthetic source (e.g., coal, shale, or tar sands bitumen) without further purification or treatment. Examples of unrefined oils include a shale oil obtained directly from a retorting operation, a petroleum oil obtained directly from distillation, or an ester obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

This invention may be further understood by reference to the following examples which are not intended to restrict the scope of the appended claims.

PREPARATIVE EXAMPLES

EXAMPLE A

Synthesis of Mixed Carbonates by Exchange Reaction

Hydroxyethyl octyl sulfide (1000 g) and dimethyl carbonate (1000 g) were placed in a 3 liter round-bottom flask. To this was added 50 g of Amberlyst A-21® catalyst (a commercial resin base). The flask was heated to about 90° C. at reflux for 1 hour. Following this, the temperature was gradually raised to 131° C. while 829 g of distillate was removed. The distillate was biphasic. The reaction flask was cooled, and a further 150 grams of dimethyl carbonate was added. This was heated to 130° C. until no further material distilled over. Analysis of the reaction product by carbon-13 nuclear magnetic resonance spectrometry showed its composition to be (% by weight): hydroxyethyl octyl sulfide, 22.1; dimethyl carbonate, 5.3; methyl, octylthioethyl carbonate, 36.6; and bis(octylthioethyl) carbonate 36.0.

EXAMPLE B

Vacuum Stripping of Mixed Carbonates

The product of the Example A was placed in a round-bottom flask equipped with a thermometer, magnetic stirring and connected to a mechanical vacuum pump and a dry ice-cooled condenser. A vacuum of less than 1 mm mercury was applied while the contents of the flask were stirred and heated to 100° C. The temperature was slowly increased to 140° C. Analysis of the reaction product by carbon-13 nuclear magnetic resonance spectrometry showed its composition to be (% by weight): hydroxyethyl octyl sulfide, 17.7; dimethyl carbonate, 3.2; methyl,octylthioethyl carbonate, 3.9; and bis(octylthioethyl) carbonate 75.2.

PERFORMANCE EXAMPLES

While the additives of this invention may possess properties other than those reported herein, the excellent antiwear properties of this invention and the additives' compatibility with conventional antioxidants are demonstrated by the following examples.

An automatic transmission fluid (ATF) formulation was prepared containing a lubrication oil basestock and conventional amounts of borated succinimide dispersant, diphenyl amine antioxidant, tolyl triazole corrosion inhibitor, amide and ethoxylated amine friction modifiers, polyalkyl-methacrylate viscosity improver, and antifoamant. To this fluid was added 0.7 wt % of the additive of Example A.

FZG—Wear Test

The foregoing ATF formulation was run in the FZG Gear Test, according to the DIN 51354 (Germany) test procedure. Accordingly, the gear set was run at increasing load stages until scoring of a gear tooth occurred. Therefore, gear failure using the formulation at higher load stages is desirable. The foregoing formulation containing the additive of Example A was measured to have a stage failure of 13 which is the maximum load stage possible using the FZG test. Thus, the result of this test illustrates that the additives of this invention are capable of providing potent antiwear performance in the absence of phosphorus as evidenced by the high FZG load stages measured.

ABOT—Oxidation Test

The antioxidative compatibility of this invention with the diphenyl amine antioxidant was demonstrated using the Ford Aluminum Beaker Oxidation Test ("ABOT") described in the Ford MERCON specification (24 Aug. 1992 revision). The ABOT results recorded at 300 hours were:

Aluminum Strip: no varnishing
Copper Strip: Grade 3B
Total Acid Number: 8.38
Viscosity @40° C.: 55.32
Brookfield Viscosity @–40° C.: 33,600
Total Acid Number Change: 6.69
% IR Change: 47.72
% Viscosity Increase: 88.39
% Pentane Insolubles: 0.45

The foregoing results, although not optimized to pass the stringent antioxidency requirements of the current Ford Mercon Specification, are important because they show that the additives of this invention have no adverse or detrimental effect on the oxidizability of the ATF.

What is claimed is:

1. A lubricating oil composition comprising:

(a) a lubricating oil; and (b) an antiwear effective amount of an oil-soluble additive, wherein the additive comprises the reaction product of a carbonylating agent and an alcohol, the alcohol being at least one thioalcohol, or, at least one thioalcohol and one sulfur-free alcohol, represented by (I) or (II), where (I) and (II) are:

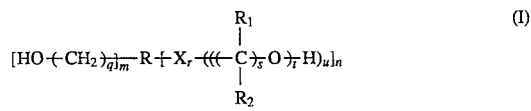

where:

m+n is an integer from 1 to 4;

m is 0 or an integer from 1 to 4;

n is 0 or an integer from 1 to 4;

q is 0 or an integer from 1 to 6;

R is a $C_1$–$C_{50}$ hydrocarbyl group in structure (I), and is a $C_1$–$C_{50}$ hydrocarbyl group or hydrogen in structure (II);

X is sulfur, oxygen, nitrogen, or —$CH_2$—;

r is 0, or an integer from 1 to 5 providing when X is oxygen or nitrogen, r is 1, when X is sulfur, r is 1 to 3, when X is —$CH_2$—, r is 1 to 5;

s is 0, or an integer from 1 to 5;

t is 0, or an integer from 1 to 12;

u is 0, or an integer from 1 to 2 providing when X is sulfur, oxygen, or —$CH_2$—, u is 1, when X is nitrogen, u is 1 or 2;

y is 0, or an integer from 1 to 10; and $R_1$ and $R_2$ are independently a $C_1$–$C_6$ alkyl, cycloalkyl, aryl, $C_1$–$C_6$ alkyl-substituted aryl, or hydrogen.

2. The composition of claim 1, wherein the carbonylating agent is dimethyl carbonate or diethyl carbonate.

3. The composition of claim 2, wherein the alcohol is selected from the group consisting of (IV), (V), and mixtures thereof, where (IV) and (V) are:

$$A—OH \qquad (IV)$$

and $$OH-B-OH \quad (V)$$

where:

A is $$\underset{X_1}{\overset{Y_1}{CH}}-(OCH_2CH_2)_v- \text{ or } Y_1-\underset{X_1}{CH}-(OCH_2CH)_{\overline{v}}\,;\; \underset{CH_3}{|}$$

$X_1$ is H;

$Y_1$ is $$R_4SCH_2-, \; R_4S\underset{CH_3}{\overset{|}{C}}HCH_2-, \; R_4S\underset{\underset{CH_3}{|}}{\overset{|}{C}HCH_2-},$$

$$R_4S\underset{CH_3}{\overset{|}{C}}H-, \; R_4SCH_2\underset{CH_3}{\overset{|}{C}}H-, \; \text{or } R_4SCH_2\underset{\underset{CH_3}{|}}{\overset{|}{C}H-};$$

v is 0 or an integer from 1–12;
B is $-CH_2CH_2SCH_2CH_2-$, $-CH_2CH_2SSCH_2CH_2-$ or $$R_5\overset{|}{C}HCH_2SR_6-;$$

where $R_4$ and $R_5$ are the same or different and are H or a hydrocarbyl group containing up to 50 carbon atoms; and $R_6$ is a hydrocarbyl group containing up to 50 carbon atoms.

4. The composition of claim 3, where A is $R_4SCH_2CH_2-$, $R_4$ is a $C_1-C_{15}$ alkyl.

5. A lubricating oil composition comprising:
   (a) a lubricating oil; and
   (b) an antiwear effective amount of an additive comprising the structure (III):

$$R-S_r+C)_{\overline{s}}O-\overset{O}{\overset{||}{C}}-O-R_3 \quad (III)$$
$$\underset{R_2}{\overset{R_1}{|}}$$

where:
   R is alkyl or aryl, or $C_1$ to $C_{10}$ alkyl-substituted aryl;
   r is 1 to 3;
   $R_1$, and $R_2$ are independently hydrogen, $C_1-C_6$ alkyl, cycloalkyl, aryl, or $C_1-C_6$ alkyl-substituted aryl;
   s is an integer from 1 to 5; and
   R3 is $C_1-C_{30}$ alkyl or $$+C)_{\overline{s}}S_r-R.$$
$$\underset{R_2}{\overset{R_1}{|}}$$

6. The composition of claim 5, where R is $C_6-C_{14}$ alkyl, r is 1, $R_1$ and $R_2$ are hydrogen, s is 2, and $R_3$ is methyl.

7. The composition of claim 5, where $R_3$ is $$+C)_{\overline{s}}S_r-R.$$
$$\underset{R_2}{\overset{R_1}{|}}$$

8. The composition of claim 1 or claim 5, wherein additive (b) is present in an amount up to 1.0 weight percent of the total composition.

9. The lubricating oil composition of claim 1 or claim 5 containing from about 0.2 to 50 weight percent based on active ingredient of additive (b).

10. A method of lubricating metal surfaces subject to mutual wear, comprising contacting said surfaces with the lubricating composition of claim 1 or claim 5.

11. A lubricating oil composition comprising:
    (a) lubricating oil; and
    (b) an oil-soluble additive, wherein the additive comprises the reaction product of a carbonylating agent and an alcohol, wherein the alcohol is selected from the group consisting of (IV), (V), and mixtures thereof, where (IV) and (V) are:

$$A-OH \quad (IV)$$

and $$OH-B-OH \quad (V)$$

where:

A is $$\underset{X_1}{\overset{Y_1}{CH}}-(OCH_2CH_2)_v- \text{ or } Y_1-\underset{X_1}{CH}-(OCH_2CH)_{\overline{v}}\,;\; \underset{CH_3}{|}$$

$X_1$ is $R_4SCH_2-$;

$Y_1$ is $$R_4SCH_2-, \; R_4S\underset{CH_3}{\overset{|}{C}}HCH_2-, \; R_4S\underset{\underset{CH_3}{|}}{\overset{|}{C}HCH_2-},$$

$$R_4S\underset{CH_3}{\overset{|}{C}}H-, \; R_4SCH_2\underset{CH_3}{\overset{|}{C}}H-, \; \text{or } R_4SCH_2\underset{\underset{CH_3}{|}}{\overset{|}{C}H-};$$

v is 0 or an integer from 1–12;
B is $-CH_2CH_2SCH_2CH_2-$, $-CH_2CH_2SSCH_2CH_2-$ or $$R_5\overset{|}{C}HCH_2SR_6-;$$

where $R_4$ and $R_5$ are the same or different and are H or a hydrocarbyl group containing up to 50 carbon atoms; and $R_6$ is a hydrocarbyl group containing up to 50 carbon atoms.

* * * * *